United States Patent [19]

Sierra et al.

[11] Patent Number: 5,290,552

[45] Date of Patent: Mar. 1, 1994

[54] SURGICAL ADHESIVE MATERIAL

[75] Inventors: David H. Sierra, San Jose; Edward E. Luck; Dennis M. Brown, both of Menlo Park, all of Calif.

[73] Assignee: Matrix Pharmaceutical, Inc./Project Hear, Menlo Park, Calif.

[21] Appl. No.: 855,921

[22] Filed: Mar. 23, 1992

Related U.S. Application Data

[63] Continuation-in-part of Ser. No. 627,561, Dec. 10, 1990, abandoned, which is a continuation of Ser. No. 512,098, Apr. 10, 1990, abandoned, and a continuation of Ser. No. 189,187, May 2, 1988, abandoned.

[51] Int. Cl.$^5$ ................... A61K 35/16; A61K 37/547
[52] U.S. Cl. ................... 424/94.64; 424/530; 424/423; 514/801; 514/21; 514/561
[58] Field of Search ................... 424/530, 423, 94.64; 514/801, 21, 561

[56] References Cited

U.S. PATENT DOCUMENTS

| | | | |
|---|---|---|---|
| 3,949,073 | 4/1976 | Daniels et al. | 514/2 |
| 4,061,731 | 12/1977 | Gottlieb | 424/530 |
| 4,627,879 | 12/1986 | Rose et al. | 106/124 |

FOREIGN PATENT DOCUMENTS 0166263 1/1986 European Pat. Off. .

Primary Examiner—Douglas W. Robinson
Assistant Examiner—Jean C. Witz
Attorney, Agent, or Firm—Bertram I. Rowland

[57] ABSTRACT

The present invention provides a surgical adhesive comprising, in an aqueous composition, fibrinogen, FXIII, collagen, thrombin, $Ca^{2+}$ and optionally, an antifibrinolytic agent. The present adhesive may be formed from the patient's plasma without the use of any added reagents for concentration or isolation of the fibrinogen. Conveniently, the adhesive is formulated as a two-part composition which is mixed together just prior to use.

21 Claims, No Drawings

SURGICAL ADHESIVE MATERIAL

CROSS-REFERENCE TO RELATED APPLICATIONS

This application is a continuation-in-part of application Ser. No. 627,561, filed Dec. 10, 1990, abandoned, which application is a continuation of application Ser. No. 512,098, filed Apr. 10, 1990, now abandoned, and application Ser. No. 189,187, filed May 2, 1988, also abandoned.

INTRODUCTION

1. Technical Field

The field of the present invention relates to surgical adhesives.

2. Background of the Invention

Early surgical adhesive formulations based on fibrinogen suffered from a number of disadvantages. The fibrin solutions ("FS") necessarily contained a high content of fibrinogen, about 8-10%, which could only be prepared from fibrinogen lyophilizates with difficulty. This so-called cryoprecipitate was relatively unstable and had to be stored at temperatures below $-20°$ C. until used. Formulations to improve the stability of the cryoprecipitate included adding inhibitors of plasminogen activator or albumin. The fibrinogen concentrates were mixed with thrombin just prior to application to the wound.

Other large scale production methods utilizing pooled plasma include precipitation by ethanol, cold neutral salts or amino acids. All are variations of commercial blood fractionation methods. These FS products are currently available in Europe only.

Other formulations of surgical adhesives had a pore structure based on collagen for covering wounds wherein a non-woven fabric consisting of collagen fibers was applied to the wound. The fabric was fixed to the wound using a fibrinogen-thrombin mixture which was applied to either the inner or outer side of the collagen fabric. However, the fibrinogen was found to coagulate rapidly and thus not to effectively penetrate into the collagen fabric.

The current formulations use patient autogenous fibrinogen glues together with thrombin. While the use of autogenous fibrinogen avoids problems with rejection of the material, the adhesives can require relatively large quantities of patient blood. Further, the processing times range from an hour to overnight, and require both the equipment and expertise of a hospital clinical blood laboratory with trained technicians. Additionally, a number of reagents are introduced into the blood to fractionate and concentrate the fibrinogen and related proteins from the plasma in some patient autogenous fibrin glue (AFG) formulations.

The cohesive and adhesive properties of FS produced by these methods are generally inconsistent and inferior to commercial product.

RELEVANT LITERATURE

U.S. Pat. No. 4,650,678 describes a solid fibrinogen formulation which contains a substance having a urea or guanidine radical to increase the solubility and viscosity of fibrinogen solutions. U.S. Pat. No. 4,600,574 describes a surgical adhesive based on a flat material consisting of collagen, gelatin or polysaccharide impregnated with a solution of fibrinogen and Factor XIII, which material is lyophilized to form a matrix.

U.S. Pat. No. 4,061,731 describes a composition comprising patient autologous plasma and microcrystalline collagen (U.S. Pat. Nos. 3,628,974 and 3,742,955) and/or gelatin in combination with endogenous thrombin to form a scar augmentation material that may be introduced intracutaneously by syringe.

U.S. Pat. No. 4,627,879 describes a single-donor sourced cryoprecipitated fibrin sealant formulation that may be used in conjunction with a microcrystalline sponge (U.S. Pat. Nos. 3,628,974 and 3,742,955).

SUMMARY OF THE INVENTION

The present invention provides a surgical adhesive comprising an aqueous composition, a source of fibrinogen, and Factor XIII (FXIII), e.g., plasma, particularly patient autologous plasma, collagen, thrombin, and optionally, an antifibrinolytic agent. The present adhesive is formed from plasma without the use of any added reagents for concentration or isolation of the fibrinogen. Conveniently, the adhesive is formulated as a two-part composition which is mixed together just prior to use. Fibrinogen with FXIII from any source or derived by any method may be used as well.

DESCRIPTION OF SPECIFIC EMBODIMENTS

A surgical adhesive using patient fibrinogen and FXIII, conveniently from plasma, particularly patient autologous plasma, in conjunction with collagen and thrombin is provided. The plasma can be used directly or as a plasma cryoprecipitate in which the fibrinogen has been concentrated without the use of any added reagents, or any fibrinogen and FXIII composition can be used.

The surgical adhesive comprises in an aqueous composition a source of fibrinogen and FXIII, particularly plasma, collagen in an amount sufficient to thicken the composition, thrombin in an amount sufficient to catalyze polymerization of fibrinogen present in the composition and $Ca^{2+}$ and, optionally, an antifibrinolytic agent in amount sufficient to retard degradation of the resulting adhesive clot. The surgical adhesive is conveniently formulated as a two-part composition in which fibrinogen/FXIII and collagen constitute the first component, and thrombin together with an antifibrinolytic agent, and $Ca^{2+}$ constitute the second component.

Plasma provides a source of fibrinogen which constitutes the adhesive component of the composition. Conveniently, the plasma may be obtained from the patient for which the surgical adhesive is to be used. The plasma can be used "as is" after standard preparation which includes centrifuging out cellular components of blood. Alternatively, the plasma can be further processed to concentrate the fibrinogen to prepare a plasma cryoprecipitate. The plasma cryoprecipitate can be prepared by freezing the plasma for at least about an hour at about $-20°$ C., and then storing the frozen plasma overnight at about 4° C. to slowly thaw. The thawed plasma is centrifuged and the plasma cryoprecipitate is harvested by removing approximately four-fifths of the plasma to provide a cryoprecipitate comprising the remaining one-fifth of the plasma. Other fibrinogen/FXIII preparations may be used, such as cryoprecipitate, patient autologous fibrin sealant, fibrinogen analogs or other single donor or commercial fibrin sealant materials. Approximately 0.5 ml to about 1.0 ml of either the plasma or the plasma-cryoprecipitate provides about 1 to 2 ml of adhesive composition which is sufficient for use in middle ear surgery. Other plasma proteins (e.g., albumin, plasminogen, von Willebrands factor, Factor VIII, etc.) may or may not be present in the fibrinogen/FXII separation due to wide variations in the formulations and methods to derive them.

Collagen, preferably hypoallergenic collagen, is present in the adhesive in an amount sufficient to thicken the adhesive composition and augment the cohesive properties of the adhesive preparation.

The collagen may be atelopeptide collagen or telopeptide collagen, e.g., native collagen. In addition to thickening the composition, the collagen augments the fibrin by acting as a macromolecular lattice work or scaffold to which the fibrin network adsorbs. This gives more strength and durability to the resulting glue clot with a relatively low concentration of fibrinogen in comparison to the various concentrated autogenous fibrinogen glue formulations (i.e., AFGs).

The form of collagen which is employed may be described as at least "near native" in its structural characteristics. It may be further characterized as resulting in insoluble fibers at a pH above 5; unless crosslinked or as part of a complex composition, e.g., bone, it will generally consist of a minor amount by weight of fibers with diameters greater than 50 nm, usually from about 1 to 25 volume % and there will be substantially little, if any, change in the helical structure of the fibrils. In addition, the collagen composition must be able to enhance gelation in the surgical adhesion composition.

The gelation enhancement effect requires a collagen preparation that has the following characteristics: (a) is flowable or capable of being flowable; (b) increases the viscosity of fibrinogen solutions; (c) decreases the gelation time of fibrinogen solutions upon the addition of thrombin when compared to equivalent concentrations of neat fibrinogen (i.e., decreases the thrombin concentration necessary to enact gelation at a given rate), (d) decreases the critical fibrinogen concentration necessary to form a cohesive gel; and (e) increases or improves the material cohesive mechanical properties when compared to a gel formed from a neat solution with equivalent fibrinogen concentration.

A number of commercially available collagen preparations may be used. Zyderm Collagen Implant ® ("ZCI") has a fibrillar diameter distribution consisting of 5 to 10 nm diameter fibers at 90% volume content and the remaining i? % with greater than about 50 nm diameter fibers. ZCI is available as a fibrillar slurry and solution in phosphate buffered isotonic saline, pH 7.2, and is injectable with fine gauge needles.

As distinct from ZCI, cross-linked collagen available as Zyplast ® may be employed. Zyplast ® is essentially an exogenously crosslinked (glutaraldehyde) version of ZCI. The material has a somewhat higher content of greater than about 50 nm diameter fibrils and remains insoluble over a wide pH range. Crosslinking has the effect of mimicking in vivo endogenous crosslinking found in many tissues.

Bovine tendon suspension exhibits solubility characteristics similar to Zyplast ®, but includes a fraction of fibrils of macroscopic diameter and length. The collagen is highly crosslinked.

Finally, one may use bone powder, particularly human bone powder, comprising polydisperse particulates ranging from about 200–300 μm in size and in addition to collagen comprise hydroxyapatite, tricalcium phosphate and fluoroapatite. Also, fibrous collagen analogs may be incorporated as an adjuvent or substitute for native or near native state fibriller collagen.

Further descriptions of collagen preparations useful in the subject invention are found in U.S. Pat. No. 4,233,360.

The collagen will normally be in a liquid vehicle which is physiologically acceptable, particularly an aqueous isotonic medium, desirably an aqueous medium at about physiologic salt concentration.

The amount of the collagen can be varied to provide adhesives of differing viscosities and strengths, depending on the particular application for the adhesive. Usually, the collagen is a flowable composition dispersed in phosphate buffered saline to provide a final concentration in the adhesive formulation of at least about 5 mg/ml, usually from about 5 mg/ml to about 50 mg/ml, more usually about 10 mg/ml to about 50 mg/ml, most usually about 10 to 40 mg/ml.

Thrombin acts as a catalyst for fibrinogen to provide fibrin, an insoluble polymer. Thrombin is present in the surgical adhesive in an amount sufficient to catalyze polymerization of fibrinogen present in the patient plasma. Thrombin also activates FXIII, a plasma protein that catalyzes covalent crosslinks in fibrin, rendering the resultant clot insoluble. Usually the thrombin is present in the adhesive composition in concentration of from about 0.01 to about 1000 or greater NIH units (NIHu) of activity, usually about i to about 500 NIHu, most usually about 200 to about 500 NIHu. The thrombin can be from a variety of host animal sources, conveniently bovine. Thrombin is commercially available from a variety of sources including Parke-Davis, usually lyophilized with buffer salts and stabilizers in vials which provide thrombin activity ranging from about 1000 NIHu to 10,000 NIHu. The thrombin is usually prepared by reconstituting the powder by the addition of either sterile distilled water or isotonic saline. Alternately, thrombin analogs or reptile-sourced coagulants may be used.

The fibrinogen, thrombin, FXIII or other natural protein used in the subject composition may be substituted by other naturally occurring or synthetic compounds or compositions which fulfill the same functions, e.g. a reptilase coagulation catalyzed, for example, ancrod, in place of thrombin.

Usually the surgical adhesive will additionally comprise an effective amount of an antifibrinolytic agent to enhance the integrity of the glue clot as the healing processes occur. A number of antifibrinolytic agents are well known and include aprotinin, C1-esterase inhibitor and ε-amino-n-caproic acid (EACA). ε-amino-n-caproic acid, the only antifibrinolytic agent approved by the FDA, is effective at a concentration of from about 5 mg/ml to about 40 mg/ml of the final adhesive composition, more usually from about 20 to about 30 mg/ml. EACA is commercially available as a solution having a concentration of about 250 mg/ml. Conveniently, the commercial solution is diluted with distilled water to provide a solution of the desired concentration. That solution is desirably used to reconstitute lyophilized thrombin to the desired thrombin concentration.

The surgical adhesive material can serve as a vehicle for a wide variety of components which may impact desireable physical, chemical, biological and/or therapeutic advantages. These components may be mixed with collagen, plasma, thrombin or combination thereof, or with the final material, depending on the nature of the additive, rate of gelling, interaction between components, and the like.

Various components may be added which serve to recruit or expand the leukocyte or endothelial population, inhibit pathways of leukocytes, endothelial cells or the like, or impact novel peptides.

Compounds of biological interest include growth factors, e.g. EGF, TGF-$\alpha$, TGF-$\beta$, TGF-I and TGF-II, FGF, PDGF, etc.; eytokines, e.g. IFN-$\alpha$, -$\beta$, -2, IL-2, IL-3, IL-6, stud factor, hematopoietic factor, etc. immunoglobulins; metabolic substances, e.g. insulin, corticosteriods, hormones, etc. Other materials include structural materials, such as physiologically acceptable alloplastic materials, e.g. polymers, glasses, metals, ceramics, composites thereof, etc.

The surgical adhesive material may be mixed with cells, autologous, cultured or modified, allogeneic or xenogeneic, such as epithelial, epidermal, fibroblast, osteoblast, mesenchymal, hepatic (hepatocytes), pancreatic (e.g. macrophage platelet, T-cell, B-cell, granulocytes, monocytes, etc., or cultured modified cells to deliver therapeutic or growth enhancing substances.

For dental or orthopedic applications, inorganic minerals or a mixture of inorganic minerals, naturally occurring or synthetic, desirably hydroxyapatite or minerals found in bone powder or chips may be added to the formulation, most conveniently to the plasma fraction of component 1 (plasma plus collagen). The mineral(s) are present in a volume ratio to the collagen component of from about 1:2 to about 4:1 depending upon the desired flow characteristics or intended use and site. Additionally, viable osteoblasts may be harvested from a donor site and incorporated into the composition, conveniently in component 1, for use in transplantation. Other bone restorative materials in particulate form may be used. Among the alloplastic materials are polylactic and poly-glycolic acids, polymethycrylate, poly-HEMA, bioglass, cerevital and other glasses, Al, Ti, CoCr and other metals, $Al_2O_3$ and other ceramics, etc. and combinations and composites thereof. They may be used in the same volume to volume ratios as for bone mineral. Other restorative materials such as proteinaceous particles or beads made from collagen, fibrin (ogen), albumin, etc., may be used as well, depending upon the tissue repair site. Liposomes may also be incorporated.

The surgical adhesive may additionally contain an antibiotic. The antibiotic may be incorporated into the collagen component if the antibiotic is a liquid. Alternatively, the antibiotic may be suspended in the plasma fraction of component 1 if it is in powder form. The therapeutic dose levels of a wide variety of antibiotics for use in drug release systems are well known. See for example, *Collagen*, Vol. III, Biotechnology; Marcel E. Nimni, Ph.D., Editor, CRC Press, Inc. (1988) pp. 209-221, and the references cited therein and *Biomaterials*, G. D. Winter, D. F. Gibbons, H. Plank (Eds.), John Wiley & Sons, New York (1980), pp. 669-676. Antimicrobial agents are particularly useful for compositions applied to exposed wound repair sites such as sites in the mouth or to compromised wound sites such as burns.

The surgical adhesive is conveniently formed by mixing two components just prior to use. The first component comprises the fibrogen and FXIII, usually, together with collagen. That component is conveniently prepared by mixing the fibrogen in an aqueous medium with collagen to form a substantially uniform composition under low shear conditions at ambient temperatures. Conveniently, using two syringes joined by a syringe-to-syringe connector having about a 1 mm or less diameter opening, substantial uniformity can be achieved with simple, generally available equipment. Generally, about 5 to 10 passes through the opening is sufficient. With autologous plasma, this component can be prepared during surgery or up to 8 hrs. prior to surgery, when stored at room temperature. Alternately, the plasma fraction may be collected and prepared up to one week or longer prior to mixing with the collagen fraction. The second component comprises thrombin. If an antifibrinolytic agent is present in the composition, it is usually mixed with the thrombin as part of component 2. Component 2 can be stored for about 8 hrs. at room temperature, for about 2 days at about 4° C., or for up to a week when frozen at $-20°$ C. Other adjuvants such as particulates or cells may be added to the fibrinogen/FXIII or collagen components prior to mixing.

The two components are mixed just prior to the application to the patient. The components may be formulated with concentrations that allow mixing the components in substantially equal volumes to simplify the final preparation of the adhesive. Conveniently, a dual-syringe holder with a disposable mixing tip can be used. Alternatively, the two components can be mixed using two syringes as described above, or the first component may be directly applied to the repair site by spatula or other surgical tool.

The surgical adhesive can be used in applications where prior art surgical adhesives were previously used. The material can be used as a soft tissue augmentor or soft tissue substitute in plastic reconstructive surgery. The adhesive may be also used to attach skin grafts to a recipient site without the use of sutures or with a reduced number of sutures, or as a growth matrix for transplanted intact osteoblasts in bone repair and reconstruction. The adhesive can also be used for applications such as ossicular chain reconstruction, nerve anastomosis or other situations where repair by sutures is impossible or undesirable, or as a wound dressing. The surgical adhesive may be applied in a number of ways determined by the surgical indication and technique.

The following examples are offered by way of illustration and not by way of limitation.

EXPERIMENTAL

EXAMPLE 1

Preparation of Adhesive

To prepare a preferred formulation of the adhesive composition, the following protocol was followed. Patient's blood (5 cc) was collected in a citrated vacuum blood collection tube (Vacutainer) by venipuncture. The blood was centrifuged for 10 min at 4000 rpm. About 0.5 cc plasma was removed from the Vacutainer with a 1 cc syringe. A syringe-to-syringe connector (20-gauge) was used to mix 0.5 cc fibrillar collagen with 0.5 cc patient's plasma for about 5 to 10 passes. Component 1 was then ready for use or was stored for up to about 6 to 8 hrs. at room temperature.

Component 2 was prepared by drawing 1 cc of a solution of 250 mg/ml of aminocaproic acid into a 12-cc syringe. Nine cc of water for Injection, U.S.P., was drawn in the same syringe to provide a 25 mg/ml concentration of aminocaproic acid. Two cc of that solution was added to 1000 NIH units of bovine thrombin (Thrombostat, Parke-Davis) and drawn into a 1 cc syringe. Component 2 was ready for use or was stored, as described previously.

At that point, either the two syringes were mounted into a dual-syringe dispenser/mixer or modified spinal tap needles were attached to the individual syringes to mix and apply the components.

EXAMPLE 2

Concentrations and Gelation Time Effects In Vitro

The following materials were used to determine gelation time in vitro:

purified fibrinogen from Sigma Chemical Company, bovine source, cat. #F4753, reconstituted to desired concentrations with Ringer's solution;

collagen fibrillar, native or near native state, in PBS, pH 7.0, at 35 mg/ml; and lyophilized thrombin Thrombostat by Parke-Davis, reconstituted with Sterile Water for Injection, U.S.P. to 100 NIH units per ml. (1 NIH unit (10 µl) was delivered to each test formulation.)

Human plasma was collected using citrated Vacutainers, then centrifuged for 10 min at 4000 rpm. A 1 ml test solution of each formulation was maintained at 37° C. using a circulating water bath in each assay.

Tables 1 and 2 illustrate the results. As used in the Tables, [Fibro] [collagen] indicate the concentration of clottable lyopholized fibrinogen and collagen, respectively, dissolved in Ringer's Solution and Gel time is the amount of time for gelation of the clot. The collagen and fibrinogen concentrations listed are the final concentrations in the test adhesive mixture.

TABLE 1

| PURIFIED FIBRINOGEN WITHOUT COLLAGEN | | |
|---|---|---|
| [Fibro] (mg/ml) | Gel Time (sec) | Comments |
| 5 | 19 | solid clot |
| 2.5 | 22 | solid clot |
| 1.25 | 30 | solid clot |
| 0.6 | 40 | solid clot |
| 0.3 | 50 | solid clot |
| 0.15 | 90 | fluid clot, transparent |
| 0.07 | 210 | fluid clot, fragile |
| 0.035 | 270 | fluid clot, fragile |
| 0.017 | — | no visible clot formation |

TABLE 2

| PURIFIED FIBRINOGEN WITH COLLAGEN AT 6 mg/ml | | |
|---|---|---|
| [Fibro] (mg/ml) | Gel Time (sec) | Comments |
| 2.5 | 7 | solid clot |
| 1.25 | 8 | solid clot |
| 0.6 | 9 | solid clot |
| 0.3 | 14 | solid clot |
| 0.15 | 20 | solid clot |
| 0.07 | — | no apparent clotting effect |
| 0.035 | — | no apparent clotting effect |

As demonstrated using fibrinogen without collagen (Table 1), there was some clotting effect at 0.07 and 0.035 mg/ml fibrinogen concentration. However, due to the fragility and fluidity of the resultant clots and comparison to the viscosity of a collagen-alone control using 6 mg/ml collagen, it was difficult to discern any clotting effect at these lower fibrinogen concentrations. As shown in Table 2, solid clots were achieved at fibrinogen concentrations of from 2.5 to 0.15 mg/ml using 6 mg/ml collagen.

TABLE 3

| PURIFIED FIBRINOGEN WITH COLLAGEN AT 15 mg/ml | | |
|---|---|---|
| [Fibro] (mg/ml) | Gel Time (sec) | Comments |
| 2.5 | — | instantaneous gelation |
| 1.25 | 10 | solid clot |
| 0.6 | 15 | solid clot |
| 0.3 | 25 | solid clot |
| 0.15 | 30 | solid clot |
| 0.07 | 40 | fluid and fragile clot |
| 0.035 | 45 | fluid and fragile clot |
| 0.017 | 120 | fluid and fragile clot |
| 0.008 | — | no apparent gelation |

This data demonstrated the practical limits for concentrations that can be used under these experimental conditions for reconstituted lyophilized bovine fibrinogen. In particular, compositions with concentrations of lyophilized fibrinogen as high as 2.5 mg/ml gelled instantly and were not useful. Concentrations of 0.07 mg/ml or less produced a fluid and fragile clot. Formulations using between 1.25 and 0.15 mg/ml fibrinogen together with 15 mg/ml collagen produced useful adhesive compositions. Higher concentrations than 15 mg/ml of collagen may be used successfully. However, it is difficult to objectively assess gelation time due to the limitations of current test equipment in evaluating test solutions of relatively high viscosity.

A study was performed to determine the dilutions of plasma that were sufficient for proper clot formation. The results are shown in Table 4. Other than the plasma dilution, the conditions were the same as those described for the studies illustrated in Tables 1-3.

TABLE 4

| PLASMA WITH RINGER'S AS DILUENT | | | |
|---|---|---|---|
| Plasma ml | Ringer's ml | Gel Time sec | Comments |
| 1.0 | 0 | 15 | solid clot |
| 0.75 | 0.25 | 12 | solid clot |
| 0.5 | 0.5 | 20 | solid clot |
| 0.33 | 0.67 | 30 | fluid clot |
| 0.25 | 0.75 | 35 | fluid clot |
| 0.12 | 0.87 | — | no gelation, small clots |

The purpose of this next study was to compare the effect of various plasma dilutions. Since one is, in essence, diluting the plasma with collagen to form the adhesive, the effect of collagen in comparison to buffer solution as diluent on gelation time and clot quality was studied. Plasma was mixed with fibrillar collagen (35 mg/ml) native in a flowable state to determine useful ranges of plasma fibrinogen concentrations.

TABLE 5

| PLASMA WITH ZCI COLLAGEN AT A CONCENTRATION OF 35 mg/ml | | | | |
|---|---|---|---|---|
| Plasma (ml) | Collagen (ml) | [Collagen] (mg/ml) | Gel Time (sec) | Comments |
| 0.75 | 0.25 | 8.75 | 15 | * |
| 0.5 | 0.5 | 17.5 | 10 | solid clot |
| 0.33 | 0.67 | 23.1 | 30 | solid clot |
| 0.25 | 0.75 | 26.2 | 100 | fluid clot |

*Collagen congealed into a small clot within the gel, which was difficult to evaluate.

As shown in Table 5, combining volumes of plasma with 35 mg/ml collagen in ratios between about 1:1 to about 1:2 plasma:collagen produced useful adhesives. This study demonstrated that the presence of collagen as a plasma "diluent" actually allows plasma fibrinogen to form a solid clot at lower fibrinogen concentrations than plasma fibrinogen at the same concentration but without collagen.

Gelation of surgical adhesive material (SAM) formulations with fibrillar collagen concentrations greater than 20 mg/ml is difficult to determine due to the high viscosity of the test solution. The highest concentration was at 32 mg/ml in both plasma and purified bovine fibrinogen (1.5 mg/ml fibrinogen concentration for both) under standard test conditions. The gelation times were 8 and <1 seconds, respectively, These observations do not preclude the use of collagen concentrations greater than 30 mg/ml. Samples have been successfully produced with collagen concentrations as high as 60 mg/ml with as little as 1.5 mg/ml fibrin concentration. Higher collagen concentrations could be used with higher fibrinogen concentrations.

All test preparations were flowable, moldable viscoelastic fluids capable of being extended through syringe hubs and/or needles prior to the addition of thrombin.

TABLE 6

EFFECT OF COLLAGEN PREPARATION AND BUFFER CONDITION ON GELATION TIMES

| Sample ID # | Buffer (mM) [Na+] | [Cl−] | [PO$_4^3$] | Preparation Method | Other Treatments | Collagen Source | Telopeptides | Fiber diameter >5 μm | net charge @ pH 7.2 | gel time (seconds) |
|---|---|---|---|---|---|---|---|---|---|---|
| 1 | 150 | 130 | 20 | Luck et al.; #4, 233, 360 | none | corium | no | yes | physiologic | <1 |
| 2 | 150 | 130 | 20 | Luck et al.; #4, 233, 360 | GTA x-linked | corium | no | yes | physiologic | <1 |
| 3 | 150 | 130 | 20 | Daniels et al.; #3, 949, 073 | none | corium | no | no | physiologic | >300 |
| 4 | 150 | 130 | 20 | Daniels et al.; #3, 949, 073 | incubated @ 37° C. > 2 h | corium | no | yes | physiologic | <1 |
| 5 | 236 | 68 | 100 | Daniels et al.; #3, 949, 073 | hypertonic | corium | no | no | physiologic | >300 |
| 6 | 236 | 68 | 100 | Daniels et al.; #3, 949, 073 | incubated @ 37° C. > 2 h | corium | no | yes | physiologic | >300 |
| 7 | 150 | 130 | 20 | * | none | tendon | no | yes | physiologic | <1 |
| 8 | 150 | 130 | 20 | * | GTA x-linked | tendon | no | yes | physiologic | <1 |
| 9 | 150 | 130 | 20 | Miyata et al.; #4, 164, 559 | succinylated | corium | yes | no | negative | >300 |
| 10 | 150 | 130 | 20 | Miyata et al.; #4, 164, 559 | succinylated, substituting collagen source | tendon | no | yes | negative | >300 |
| 11 | 150 | 130 | 20 | +Battista; #3, 628, 974, and #3, 742, 955 | ionized HCL salt | corium | yes | yes | ? | 30 |
| 12 | 150 | 130 | 20 | * | contains bone minerals | cancellous bone | yes | yes | physiologic | <1 |

*process details not available (trade secret)
+collagen product described in: Gottlieb; #4, 061, 731 Rose et al.; #4, 627, 879

From the data, we conclude that for gelation enhancement to take place, the collagen would appear to be defined by a relatively narrow set of specifications, the collagen preparation must contain some significant precentage of fibers that are insoluble in the pH ranges useful for treatment in physiological conditions (>pH 5) and have a fiber diameter of 5 μm or greater. The collagen must be native (containing telopeptide ends) or near-native (lacking telopeptides). Treatments other than crosslinking would appear to inhibit gelation enhancement, such as succinylation (Miyata, et al.), or ionization processing. The solvent conditions dictate physiologic or near physiologic pH and ionic strength. The formulations will gel under non-physiologic conditions, however, at much slower rates.

EXAMPLE 4

Clot Stability In Vitro

One ml of adhesive material was placed in about 30 ml of Ringer's solution and allowed to sit undisturbed at 37° C. until the clot dissolved in its entirety. The adhesive materials compared were:

1–0.5 ml human plasma+0.5 ml fibrillar collagen+100 NIH units bovine thrombin in 1 ml of 25 mg/ml ε-aminocaproic acid;

2–0.5 ml human plasma+0.5 ml fibrillar collagen+100 NIH units bovine thrombin in 1 ml of Sterile Water for Injection, U.S.P.;

3–1.0 ml human plasma+100 NIH units bovine thrombin in 1 ml Sterile Water for Injection, U.S.P.

EXAMPLE 3

Effect of Collagen Preparation on Gelation Enhancement Effect

Experiments were performed to evaluate the effect of collagen preparation on gelation times of purified bovine fibrinogen solutions. Test conditions were those of Example 2 with the following notes:
[collagen]: 15–20 mg/ml
[fibrinogen]: 1.5 mg/ml
[thrombin]: 1 U/ml
pH: 7.2
[Ca$^{2+}$]: 20 mM

EXAMPLE 5

Viscosity of Fibrinogen, Collagen and Composite Solutions. Prepolymerized

Studies were performed to evaluate the viscosity characteristics of fibrinogen, collagen and SAM formulations prior to the addition of thrombin. The purpose of these studies was to investigate the interaction of collagen with fibrinogen prior to polymerization. This is an important parameter to evaluate as flow characteristics will dictate the ease of delivery as well as cohesiveness of a bolus of the material once delivered to a repair site and prior to the addition of thrombin. Preparations of low viscosity will be more likely to migrate from the repair site as well as be less amenable to further molding and shaping.

Samples were prepared and evaluated on a Brookfield cone and plate viscometer with data analysis software on a personal computer. The test conditions were:
temperature: 20° C. (±0.2° C.)
ω range: 0.8 to 225 s$^{-1}$
ω reported: 8.2 s$^{-1}$
[Na$^+$]: 150 mM
[Cl$^-$]: 130 mM
[PO$_4^{3-}$]: 20 mM
pH: 7.2
collagen preparation: Luck et al., U.S. Pat. No. 4,233,360

The fibrinogen preparations demonstrated an increase in viscosity and shear stress with increasing fibrinogen concentration. Both solutions tested were ilatant (shear thickening) with respect to shear rate. Neither plasma nor cryoprecipitate of 22.5 mg/ml could be tested because of their viscosities being too low to detect with this system.

The fibrillar collagen had a much higher viscosity (1950 cps) and shear stress than the FS preparations (160.9 dyn/cm$^2$) at the shear rate reported. Also, it demonstrated pseudoplastic ("shear thinning") behavior with respect to shear rate, quite the opposite of that of the FS solutions.

Upon mixing the fibrillar collagen with the cryoprecipitate, the viscosity and shear rates undergo an unexpected synergistic increase, much greater than the expected additive increase in viscosity (~2900, calculated vs. 3662 cps) and shear stress (~145 vs. 302 dyne/cm$^2$). The SAM formulation incorporating plasma exhibited an even higher viscosity (4423 cps) and shear stress (364.9 dyn/cm$^2$) than the collagen-cryoprecipitate or concatenate mixture. None of the fibrinogen and SAM preparations exhibited significant thixotropy at 8.2 s$^{-1}$ (all <18% @60 minutes).

Mixtures incorporating the collagen of Battista (Avitene ®) could not be reliably tested for viscosity measurements due to significant thixotropy (98% loss of viscosity).

In conclusion, it appears the inclusion of collagen matching the specifications outlined in Table 7 will effect an unexpected increase in viscosity and shear stress that is stable over time.

TABLE 7

VISCOSITY OF FIBRINOGEN, COLLAGEN AND COMPOSITE MIXTURES PREPOLYMERIZED

| Sample ID # | Fibrinogen Source | [fibrinogen] (mg/ml) | [collagen] (mg/ml) | η | F | Viscosity Characteristics |
|---|---|---|---|---|---|---|
| 1 | cryoprecipitate | 45 | — | 47.6 | 3.9 | dilatant |
| 2 | purified | 120 | — | 142.7 | 11.8 | dilatant |
| 3 | — | — | 32 | 1950 | 160.9 | pseudoplastic |
| 4 | cryoprecipitate | 22.5 | 32 | 3662 | 302.1 | pseudoplastic |
| 5 | plasma | 1.5 | 32 | 4423 | 364.9 | pseudoplastic |

η: viscosity in centipoise
F: shear stress in dyne/cm$^2$

EXAMPLE 6

Shear Mechanical Properties

The shear (torsinal) viscoelastic mechanical properties of polymerized SAM and FS were characterized by molding specimens of different formulations into discs and evaluated on a thermostated plazek disc apparatus (Rheometrics). Test conditions were:
% strain: 10%
strain rate: 0.1 to 800 Hz
temperature: 24° C.
[thrombin]: 1 U/ml
[EACA]: 20 mg/ml
[Ca$^{2+}$]: 20 mM
Incubation (polymerization) time: 24 h before test

TABLE 8

VISCOELASTIC PROPERTIES OF SAM AND FS

| | mg/ml | | [total protein] | G' | | G'' | | η* | | tanδ | | | G* (% strain) | |
|---|---|---|---|---|---|---|---|---|---|---|---|---|---|---|
| Sample # | [fibrin] | [collagen] | | 0.1 Hz | 800 Hz | 0.1 Hz | 800 Hz | 0.1 Hz | 800 Hz | 0.1 Hz | 800 Hz | ωc | 0% | 100% |
| 1 (SAM) | 1.5* | 18 | 19.5 | 6.2 | 17 | 2 | 3 | 25 | 0.50 | 0.18 | 0.18 | — | — | — |
| 2 (SAM) | 15+ | 18 | 33 | 20 | 33 | 3.7 | 8 | 44 | 0.75 | 0.08 | 0.28 | 250 | 25 | 12 |
| 3 (FS) | 15+ | 0 | 15 | 2 | 5 | 0.17 | 0.8 | 15 | 0.25 | — | — | — | — | — |
| 4 (FS) | 30+ | 0 | 30 | 5.5 | 15 | 1.6 | 4 | 24 | 0.20 | 0.24 | 0.39 | 5 | 13 | 0.3 |

All values are dyn/cm$^2$ × (10$^2$), unless noted
*plasma fibrin source
+cryoprecipitate firbin source
ωc critical frequency in Hz
G': storage modulus
G'': loss modulus
η*: complex viscosity
tanδ: G''/G'
G*: complex modulus The SAM formulations (samples 1 & 2) demonstrated higher storage modulus, loss modules and complex viscosity than other fibrin sealant formulations (samples 3 & 4), Samples 1 & 2 also were found to have lower tan δ than sample 4. The second SAM formulation (#2) demonstrated a higher complex modulus than the high concentration FS (#4), as well as a lower loss over strain range.

The inclusion of collagen fibers significantly alters the mechanical properties of fibrin materials. Both of the SAM formulations exhibited increases in storage loss and complex module and a decrease in tan δ when compared to FS. The SAM can thus be described as being "stronger" or "tougher" than conventional FS based on protein weight comparison. The improvement in mechanical strength could permit the use of the invention in clinical indications where FS would likely fail under mechanical stress, such as packing cerebrospinal fluid leakage in transdermal procedures or securing arterial/venous access devices.

Six replicate clots were formed for each of the four groups. One Ringer's solution control was used for a turbidity assessment.

The data shows that after 35 days, group #1 showed the least degradation, where 2 of 6 clots gave off very small amounts of flocculant material. Group #2 was the second most durable group of clots with 4 of 6 clots which gave off flocculant material Group, #3 was less stable than group #2, with 6 out of 6 clots giving off flocculant material. Group #4 showed the most degradation, with 2 out of 6 clots completely degraded and the remaining clots far more fluid and flocculant than the other groups.

EXAMPLE 7

Human Clinical Trials

Human clinical trials included 24 patients undergoing a variety of middle ear surgical procedures, as well as one neurologic procedure. The 24 cases were broken down into two phases. Phase I incorporated the use of patient autologous plasma cryoprecipitate with collagen, thrombin and an anti-fibrinolytic agent. Twenty-one subjects were assigned to this first phase. Phase II incorporated the use of patient autologous citrated plasma (without any fibrinogen concentration) with collagen, thrombin and antifibrinolytic.

Patients. Thirty patients, sixteen male and fourteen female with an average age of 41 years (range 9 to 68 years) were enroled in the study. They were candidates for a range of otologic and head and neck neurologic procedures requiring conventional repair and closure techniques. Patient participation in this study was voluntary and informed consent was obtained. Patients with a known hypersensitivity to bovine source products were excluded.

Investigational Materials. SAM is comprised of two components, the first, fibrous collagen compounded with patient autologous fibrinogen, the second, a bovine thrombin reconstituted in a dilute $CaCl_2$ and e-aminocaproic acid solution. Two formulations of the SAM which differed in fibrinogen concentration were evaluated (Table 9).

TABLE 9

| SURGICAL ADHESIVE MATERIAL FORMULATIONS | | |
|---|---|---|
| Formulation | Fibrinogen (mg/ml) | Fibrinogen Source |
| I | 15 | cryoprecipitate |

TABLE 9-continued

| SURGICAL ADHESIVE MATERIAL FORMULATIONS | | |
|---|---|---|
| Formulation | Fibrinogen (mg/ml) | Fibrinogen Source |
| II | 1.5 | plasma |

The fibrous collagen (18 mg/ml) is mixed with patient autologous fibrinogen (1.5 or 15 mg/ml, nominal concentration). This mixture is then combined with thrombin (200 units/ml) reconstituted in a solution of $CaCl_2$ (0.6%) and e-aminocaproic acid (25 mg/ml) as a protease inhibitor.

Neurologic Procedures. In neurologic cases, SAM was used primarily to close and seal the dura and cranial bone subsequent to the removal of an acoustic neuroma or the repair of an encephalocele. For acoustic neuroma procedures, after the removal of the tumor, the internal auditory canal was packed with autogenous fat and muscle coated with the SAM. This was followed by the placing of a layer over the packing, and in the case of the encephalocele repair, a piece of homograft dura was secured over the closure. In both procedures, the dura would be patched with a piece of homograft dura sealed and sutured into place, then followed by a sealing of the periphery of the patch with SAM. The objective was to obtain a cerebrospinal fluid-tight seal during closure.

Otologic Procedures. The tympanossicular chain reconstruction procedures required microsurgical techniques to repair or replace the various components of the middle ear. The SAM was used to position and hold the replacement components in the desired anatomic configuration without the use of absorbable packing. In the mastoid bone/canal wall reconstructions, the SAM was mixed with autogenous bone tissue to rebuild the middle ear and canal wall with homograft dura. This was performed after the removal of infected and damaged bone. The epithelium and tympanic membrane were fixed to the rebuilt canal and mastoid with the SAM. 1 the external ear reconstruction procedure, the meatus was enlarged and recontoured by making a series of incisions about the canal opening and removing pieces of cartilage. The skin flaps were repositioned and held in place with the SAM. The gaps between the skin flaps were also filled and contoured with the SAM.

Evaluation Procedure. Patients were evaluated weekly for four weeks after the repair procedures, then monthly for six months and yearly thereafter. In the acute phase, the treatment site was assessed for tissue reactions including erythema (redness), swelling, induration and inflammation. For neurologic procedures, the cerebrospinal fluid contenence was noted. For otologic procedures, the impact of the SAM in the reconstruction and replacement of bony elements were evaluated, as was improvement in hearing performance.

Clinical Results. A total of 30 patients were treated with both SAM formulations. A summary of the procedures and formulations used are presented (Table 10).

TABLE 10

| SUMMARY OF NEUROLOGIC AND OTOLOGIC PROCEDURES WITH SAM FORMULATIONS | | |
|---|---|---|
| | Formulation | |
| Procedure | I | II |
| Acoustic neuroma | 0 | 3 |
| Encephalocele repair | 0 | 1 |
| Tympanossicular chain repair | 19 | 2 |
| Mastoid/canal | 4 | 0 |

TABLE 10-continued
SUMMARY OF NEUROLOGIC AND OTOLOGIC PROCEDURES WITH SAM FORMULATIONS

| Procedure | Formulation I | Formulation II |
|---|---|---|
| wall repair | | |
| Ext. ear reconstruction | 1 | 0 |
| TOTAL | 24 | 6 |

The SAM was biocompatible. There were no indications of inflammation or delay in healing compared with typical closure and repair techniques. In the case of external ear reconstruction, the SAM promoted good re-epithelization between the skin flaps with no apparent scarring. The patients with tympanossicular chain repair regained hearing at rates and ranges expected for these procedures. During the procedures and in subsequent post-surgical follow-up, the adhesive was an effective fluid-tight barrier and hemostatic agent. It had good adhesive and mechanical strength, firmly holding the tissue in the desired configurations. The SAM was viscous and easily moldable and immediately set-up upon the addition of thrombin. This feature facilitated the microsurgical reconstructive and replacement techniques. The SAM reduced or obviated the need for external pressure packing, allowing for earlier observation of the post-surgical healing process.

Conclusions. Head and neck surgical procedures require a variety of techniques for the repair and replacement of damaged and missing anatomic features. In many instances, conventional repair and closure techniques are inadequate even with current microsurgical techniques due to limited accessibility of the repair sites. The pilot evaluation of SAM for neurologic and otologic procedures demonstrated the utility, flexibility and efficacy of the fibrin-based adhesive technology in a number of different clinical indications. The SAM proved to be a useful and valuable adjunct to microsurgery, acting as a tissue adhesive, fluid-tight sealant, hemostatic agent and packing material.

Post-operative follow-up for up to 3.5 years of the patients treated with SAM indicated that the SAM is biocompatible and clinically effective in a wide variety of roles. No untoward effects were observed in any of the patients. Clinical assessment of the material indicates that the use of this adhesive is a valuable addition to existing surgical techniques.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A surgical adhesive useful in treating a patient in need thereof comprising in an aqueous composition:
   (a) fibrinogen and Factor XIII (FXIII);
   (b) collagen in an amount sufficient to enhance the rate of gelatin of the adhesive, said collagen being characterized by being fibrillar, insoluble at a pH greater than about 5, flowable, having substantially the native helical structure of collagen fibrils and capable of causing gelation of the subject adhesive; and
   (c) thrombin and $Ca^{2+}$ in an amount sufficient to catalyze polymerization of said fibrinogen to produce a clot.

2. A surgical adhesive according to claim 1, further comprising an antifibrinolytic agent in an amount sufficient to retard degradation of said clot.

3. A surgical adhesive according to claim 1, further comprising an effective amount of an antimicrobial agent.

4. A surgical adhesive useful in treating a patient in need thereof comprising in an aqueous composition:
   (a) fibrinogen and FXIII;
   (b) collagen in an amount sufficient to enhance the rate of gelatin of the adhesive at a concentration of at least about 5 mg/ml, said collagen being characterized by being fibrillar, insoluble at a pH greater than about 5, flowable, having substantially the native helical structure of collagen fibrils and capable of causing gelation of the subject adhesive; and
   (c) thrombin and $Ca^{2+}$ in an amount in the range of about 1 to 1000 NIHu and sufficient to catalyze polymerization of said fibrinogen to produce a clot.

5. A surgical adhesive according to claim 4, wherein the source of said fibrinogen and FXIII is autologous plasma from said patient.

6. A surgical adhesive according to claim 4, wherein said collagen is in from about 5 to 50 mg/ml and has at least about a 90% volume content of fibers of a least 5 nm in diameter.

7. A surgical adhesive according to claim 4, wherein said collagen is in from about 5 to 50 mg/ml and up to about 90% volume content of fibers of from 5 to 10 nm in diameter, and is cross-linked.

8. A surgical adhesive according to claim 4, further comprising an antifibrinolytic agent.

9. A surgical adhesive according to claim 4, further comprising a mineral.

10. A surgical adhesive according to claim 9, wherein said mineral is a naturally occurring calcium phosphate.

11. A surgical adhesive useful in treating a patient in need thereof comprising in an aqueous composition:
   (a) fibrinogen and FXIII;
   (b) from about 10 to 30 mg/ml collagen, said collagen being characterized by being fibrillar, insoluble at a pH greater than about 6, flowable and having substantially the native helical structure of collagen fibrils and capable of enhancing gelation of the subject adhesive;
   (c) about 1 to 500 NIHu/ml thrombin;
   (d) from about 5 to about 30 mg/ml aminocaproic acid; and
   (e) $Ca^{2+}$ in at least about 5 mM.

12. A surgical adhesive according to claim 11, wherein the source of said fibrinogen and FXIII is autologous plasma from said patient.

13. A method of making a surgical adhesive for treating a patient in need thereof, said method comprising:
   (a) mixing in an aqueous medium, fibrinogen and Factor XIII with collagen in an amount sufficient to enhance the rate of gelation of said surgical adhesive, said collagen being characterized by being fibrillar, insoluble at a pH greater than about 5, flowable and having substantially the native helical structure of collagen fibrils and capable of enhancing gelation of said medium;

(b) combining said medium with thrombin and $Ca^{2+}$ in an amount sufficient to catalyze polymerization of fibrinogen present in said medium, whereby said fibrinogen is polymerized to form said surgical adhesive.

14. A method according to claim 13, wherein said collagen is present in from about 10 to 30 mg/ml; said thrombin is present in from about 1 to 500 NIHu/ml, an anti-fibrinolytic agent is present, and said aqueous medium is fibrinogen and $Ca^{2+}$.

15. A kit comprising in a first container, collagen characterized by being fibrillar, insoluble at a pH greater than about 5, flowable and having substantially the native helical structure of collagen fibrils and capable of causing gelation of a surgical adhesive; and in a second container, thrombin, optionally combined with an antifibrinolytic agent and $Ca^{2+}$.

16. A kit according to claim 15, wherein said antifibrinolytic agent is present and is ε-amino-n-caproic acid.

17. A surgical adhesive according to claim 1, further comprising singly or a combination of:
    (a) growth factors;
    (b) cytokines; or
    (c) immunoglobulins.

18. A surgical adhesive according to claim 1, further comprising singly or a combination of:
    (a) epithelial, epidemal, fibroblast, osteoblast or mesencymal cells;
    (b) hepatocytes, pancreatic cells, macrophage, platelets, T-cells, or B-cells; where the cells of groups (a) and (b) are naturally occurring, and
    (c) cultured modified cells designed to deliver therapeutic or growth enhancing substances.

19. A surgical adhesive according to claim 1, comprising a biologically active fibrinogen analog in place of fibrinogen.

20. A surgical adhesive according to claim 1, further comprising in place of thrombin, a biologically active thrombin analog or a reptilase-coagulation catalyst.

21. A surgical adhesive according to claim 1, further s comprising alloplastic materials.

* * * * *